United States Patent [19]

Murakami et al.

[11] Patent Number: 4,634,774

[45] Date of Patent: Jan. 6, 1987

[54] PROCESS FOR PREPARING 3-HYDROXY-5-METHYLISOXAZOLE

[75] Inventors: Tadashi Murakami; Kazuo Tomita, both of Hiromachi, Japan

[73] Assignee: Sankyo Company Limited, Tokyo, Japan

[21] Appl. No.: 597,170

[22] Filed: Apr. 5, 1984

[30] Foreign Application Priority Data

Apr. 12, 1983 [JP] Japan .................................. 58-63046

[51] Int. Cl.⁴ .......................................... C07D 261/12
[52] U.S. Cl. ..................................................... 548/243
[58] Field of Search ......................................... 548/243

[56] References Cited

U.S. PATENT DOCUMENTS 3,687,968 8/1972 Iwai et al. ............................ 548/243

FOREIGN PATENT DOCUMENTS 1958252 5/1971 Fed. Rep. of Germany ...... 548/243
142710 7/1980 German Democratic Rep. .................................... 548/243
1113618 5/1968 United Kingdom ................ 548/243

OTHER PUBLICATIONS

Kato, et al., "Ketene and Its Derivatives", Chem. Abst. 77:126375j.
Rahman, et al., "Reaction of α-Keto Ketene . . . ," Chem Abst. 101: 54964q.
Jacobsen, et al., "3-Hydroxyisoxazoles", Chem Abst. 101: 191881z (1984).
Kato et al, "Studies on Ketene and Its Derivatives XLVIII Reaction of Diketene with Hydroxylamine", Chem. Pharm. Bul., vol. 20 (1972) pp. 1368-1373.
Khromov, "The Oxime of Acetoacetic Acid" (β-Oximinobutyric Acid) Chem. Abstracts, 45: 2868i (1950).
Fujimoto et al, Derive d'Isoxazol. I. Sur les Reactions Entre du Dicetene et de l'Hydroxylamine ou de Quelques Acides Hydroxamiques, Chem. Pharm. Bul., vol. 13 (1965) pp. 248-252.

Primary Examiner—Glenna M. Hendricks
Attorney, Agent, or Firm—Frishauf, Holtz, Goodman & Woodward

[57] ABSTRACT 3-hydroxy-5-methylisoxazole is prepared by reacting diketene in a continuous process with hydroxylamine to give a reaction mixture containing acetoacetohydroxamic acid and then acidifying this reaction mixture as quickly as possible to produce the 3-hydroxy-5-methylisoxazole.

8 Claims, 1 Drawing Figure

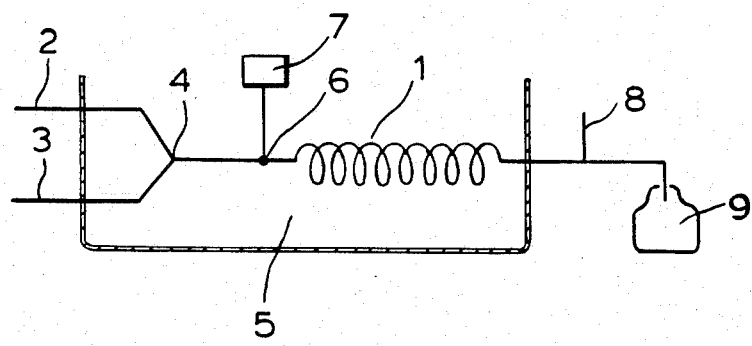

PROCESS FOR PREPARING 3-HYDROXY-5-METHYLISOXAZOLE

BACKGROUND TO THE INVENTION

The present invention relates to a process for preparing 3-hydroxy-5-methylisoxazole, which process is carried out continuously, in part or in whole, and which has a number of practical advantages.

3-Hydroxy-5-methylisoxazole has the formula (I):

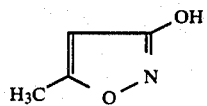

It is used as an agricultural fungicide and has a remarkable activity, particularly against soil-borne diseases.

Japanese Patent Specifications (published for opposition) Nos. 48953/74 and 9675/77 disclose methods of preparing 3-hydroxy-5-methylisoxazole (I) from diketene (II) and an O-alkyl or O-aralkyl substituted hydroxylamine (III), as illustrated in the following reaction scheme:

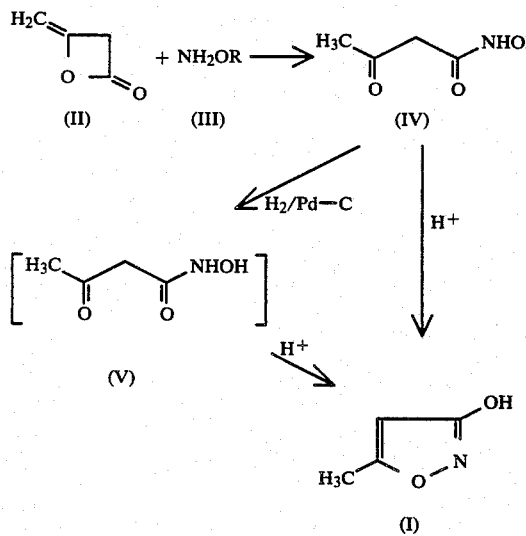

As shown in this reaction scheme, the reaction of diketene with the substituted hydroxylamine (III) gives an O-substituted acetoacetohydroxamic acid (IV). This acid (IV) is subjected to catalytic reduction followed by acidification or simply to acidification to remove the alkyl or aralkyl group represented by R and cyclise the compound, thus giving the desired 3-hydroxy-5-methylisoxazole.

Since the O-alkyl or O-aralkyl substituted hydroxylamine (III) is normally prepared from free hydroxylamine, it might appear logical from the above reaction scheme to use free hydroxylamine instead of the substituted hydroxylamine and thereby to omit the step of removing the alkyl or aralkyl group represented by R; this might be expected to give acetoacetohydroxamic acid (V) which would then cyclise to the desired 3-hydroxy-5-methylisoxazole. However, it has been established [Zhur. Obschei Khim. 20, 1858 (1950) and Chem. Pharm. Bull. 13, 248 (1965)] that the reaction of diketene with free hydroxylamine produces acetoacetic acid oxime (IX) and 3-methyl-2-isoxazolin-5-one (X). It is believed that these products are formed because the acetoacetohydroxamic acid (V) formed by the reaction is very unstable and quickly reacts with further hydroxylamine or with any nucleophilic agent present in the reaction system, as shown in the following reaction scheme:

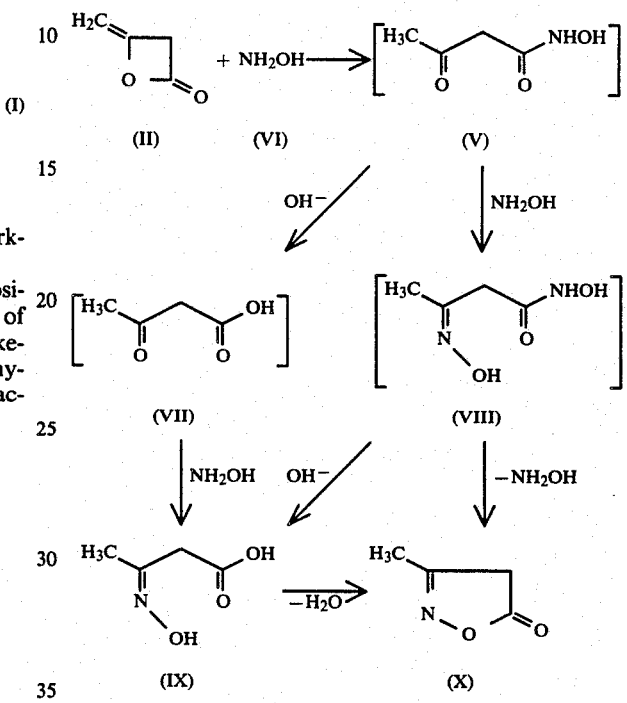

Accordingly, it has been difficult hitherto to produce 3-hydroxy-5-methylisoxazole industrially by using diketene and free hydroxylamine as the starting materials.

BRIEF SUMMARY OF INVENTION

We have now discovered that, if diketene and free hydroxylamine are reacted together in a continuous process to give a reaction mixture including acetoacetohydroxamic acid, there is a small, but definite interval (whose duration will, of course, vary depending upon the reaction conditions) during which the mixture may be acidified to yield the desired 3-hydroxy-5-methylisoxazole directly.

Thus, the present invention provides a process for preparing 3-hydroxy-5-methylisoxazole, in which diketene is reacted in a continuous process with hydroxylamine, and the reaction mixture containing acetoacetohydroxamic acid is thereafter quickly acidified to produce said 3-hydroxy-5-methylisoxazole.

BRIEF DESCRIPTION OF DRAWINGS

The accompanying drawing is a schematic illustration of apparatus which may be used to put into effect the process of the present invention.

DETAILED DESCRIPTION OF INVENTION

The reactions involved in the process of the present invention may be summarised in the following reaction scheme:

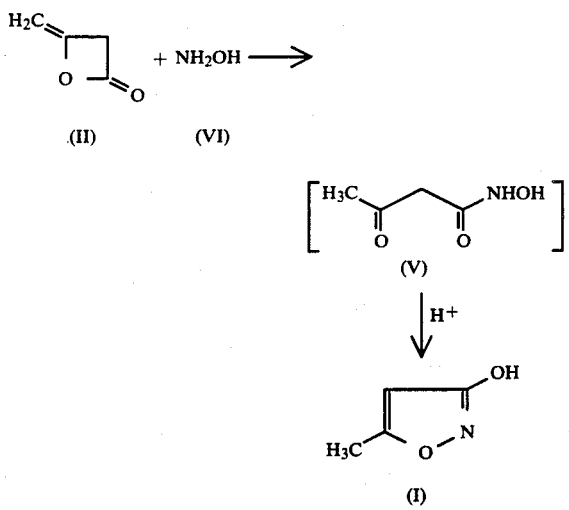

In the first stage reaction of this process, diketene (II) is reacted with hydroxylamine (VI) to give the unstable compound, acetoacetohydroxamic acid (V), in a continuous process. Quickly, to minimise side reactions, the reaction mixture is acidified, to effect cyclisation and dehydration of this acetoacetohydroxamic acid (V), and to give the desired 3-hydroxy-5-methylisoxazole (I). The process enables undesirable side reactions to be minimised and produces the desired product in a high yield, both of which are advantageous from the industrial viewpoint.

In order to carry out the process of the invention, it is preferred to feed diketene and hydroxylamine continuously to a mixer-reaction tube. A typical example of apparatus which may be employed in the process of the invention is illustrated in the accompanying drawing. To wit, diketene and hydroxylamine are continuously fed through the feeding tubes 2 and 3, respectively, of a Y-shaped mixer-reaction tube 1. The reaction takes place as soon as the two reagents mix at junction 4 in a predetermined ratio. The reaction mixture then moves towards the other end of the tube 1, propelled by the continuously supplied reagents. During this time, the reaction will go towards completion. As the reaction is exothermic, the whole mixer-reaction tube 1 is placed in a cooling bath 5, and the reaction temperature is monitored by a temperature sensor 6 and a temperature indicator 7.

The reaction mixture thus continuously produced in the reaction tube 1 contains acetoacetohydroxamic acid and has to be placed under acidic conditions rapidly before side reactions can take place. This may be achieved by mixing the reaction mixture with an acid continuously fed from an acid feeding tube 8 provided at the end of the reaction tube, and then pouring the entire mixture into the reaction vessel 9, in which dehydration and cyclisation reactions take place. Alternatively, acid may have previously been fed to the reaction vessel 9, and the reaction mixture from tube 1 may be poured directly into this vessel 9, in order for the dehydration and cyclisation reactions to take place.

Free hydroxylamine has a melting point of 33° C. and hence may be used in the absence of a solvent. However, it is preferred to use it in the form of a solution. Suitable solvents for such a solution include, for example: alcohols, such as methanol, ethanol, propanol, isopropanol or butanol; dimethyl sulphoxide; ethylene glycol dimethyl ether; water; and mixtures of any two or more of these solvents. Particularly preferred are methanol and water or a mixture thereof.

Free hydroxylamine may be obtained by neutralising an acid addition salt thereof, such as the hydrochloride or sulphate, with a base in a solvent. Suitable bases include, for example: alkali metal alkoxides, such as sodium methoxide, sodium ethoxide, sodium butoxide or potassium tert-butoxide; alkali metal hydroxides, such as sodium hydroxide or potassium hydroxide; alkaline earth metal hydroxides, such as calcium hydroxide or barium hydroxide; alkali metal carbonates, such as sodium carbonate or potassium carbonate; alkali metal acetates, such as sodium acetate or potassium acetate; ammonium acetate; and organic tertiary amines, such as pyridine, trimethylamine or triethylamine. Particularly preferred are sodium hydroxide and triethylamine. Prior to use, the salt formed by neutralisation of the acid addition salt may be eliminated; alternatively, the solution or slurry obtained by reaction of a hydroxylamine salt with a base and still containing the salt produced by the reaction may be used, without separation of the salt.

Diketene may likewise be used as such or in the form of a solution in an inert solvent. Suitable solvents include, for example: alcohols, such as methanol, ethanol, propanol or butanol; aliphatic or cyclic ethers, such as diethyl ether, ethylene glycol dimethyl ether, tetrahydrofuran or dioxane; ketones, such as acetone, methyl ethyl ketone or methyl isobutyl ketone; aromatic hydrocarbons, such as benzene or toluene; chlorinated aliphatic hydrocarbons, such as methylene chloride, chloroform, carbon tetrachloride or 1,2-dichloroethane; fatty acid amides, such as dimethylformamide or dimethylacetamide; dimethyl sulphoxide; and mixtures of these solvents. Of these solvents, methanol, ethanol and ethylene glycol dimethyl ether are preferred. In particular, we prefer to use the diketene as such or as a methanolic solution.

There is no particular limitation as to the ratios of such solvents to diketene and hydroxylamine and these may be chosen over a wide range. Preferably, in each case, from 5 to 20 ml, more preferably from 12 to 15 ml, of solvent is employed for each 10 mmoles (0.01 mole) of the reagent.

There is also no particular limitation as to the ratio of hydroxylamine to diketene and these reagents may be employed over a wide range of proportions. Normally, however, equimolar amounts or a molar excess of hydroxylamine are preferred; for example, we prefer a molar ratio of hydroxylamine to diketene of from 1:1 to 2:1, more preferably from 1:1 to 1.2:1.

The reaction of diketene with hydroxylamine is exothermic, and so the reaction temperature is preferably controlled within a range of from −78° C. to +78° C., more preferably from −30° C. to +30° C. and most preferably from −15° C. to +25° C., throughout the reaction. This may be achieved by cooling the inside or the outside of the reaction tube.

The time required for the reaction will vary, depending on the number of factors, such as the solvent used, the reaction temperature and the ratio of reagents. Generally, the reaction proceeds very rapidly, and the retention period of the reagents in the reaction tube should be kept in the range of from several seconds to 1 minute, preferably from 10 to 20 seconds, by controlling the feed rate of the reagents. Too long a period of retention in the reaction tube will increase the production of the undesired isomer, 3-methyl-2-isoxazoline-5-one [compound (X) in the second of the above reaction schemes].

Instead of converting an acid addition salt of hydroxylamine to free hydroxylamine prior to the process of the invention, this conversion may be carried out in situ. Moreover, because a mixed solution of diketene and an acid addition salt of hydroxylamine is stable and will not react unless heated, it is possible to prepare such a mixed solution and feed it continuously to a reaction tube, for example as in the apparatus illustrated in the accompanying drawing, together with an alkaline solution, to form free hydroxylamine in situ, which, in turn, is reacted continuously with diketene. Any solvent may be used for the mixed solution, provided that it dissolves both diketene and the chosen acid addition salt of hydroxylamine; examples include the above-mentioned alcohols, dimethyl sulphoxide and ethylene glycol dimethyl ether, preferably methanol.

Any of the bases mentioned above may be used, although sodium hydroxide and triethylamine are preferred.

Whichever of the embodiments described above is chosen for the first stage of the reaction, the reaction mixture thus obtained contains acetoacetohydroxamic acid, which is unstable and which is, in accordance with the present invention, quickly subjected to treatment with an acid in order to effect dehydration and cyclisation.

Examples of acids which may be used for this acidification treatment include, for example: inorganic protonic acids, such as hydrogen fluoride, hydrochloric acid, hydrobromic acid or sulphuric acid, and anhydrides thereof; Lewis acids, such as boron trifluoride, boron tribromide, zinc chloride or aluminium chloride; organic acids, such as trifluoroacetic acid, p-toluenesulphonic acid or trifluoromethanesulphonic acid; and strongly acidic ion-exchange resins, such as the Amberlite (Trade Mark) resins and Naphion-H. Particularly preferred are hydrochloric acid and sulphuric acid.

The amount of acid is preferably at least 0.5 mole per mole of acetoacetohydroxamic acid theoretically produced and we prefer to use it in an amount of from 1 to 6 moles, in order to ensure the dehydration and cyclisation reactions, to minimise production of by-products and to obtain the desired product with a high purity.

The dehydration and cyclisation reactions will take place at ambient temperatures, although they will naturally be promoted by heating; however, of course, it is undesirable to heat the reaction vessel to such an extent that the reagents undergo decomposition. Accordingly, we prefer that the reaction temperature should be no greater than 80° C. and, where the reagents are to be heated, we prefer that they should be heated to a temperature of from 60° to 80° C.; alternatively, we prefer that the reaction should be effected at ambient temperature.

The time required for completion of the dehydration and cyclisation reactions will vary, depending upon a number of factors, including the nature of the acid and solvent used, the concentration of acid, the reaction temperature and so forth; it is usually from several minutes to 1 hour.

Upon completion of the reaction, the desired product may readily be separated from the reaction mixture by conventional means, for example by extraction with a solvent or by recrystallisation. If necessary, it may by further purified by recrystallisation, column chromatography or other techniques known to the art.

The process of the present invention has a variety of advantages over prior art methods, of which the principal ones are that there is no need for preparation of an O-substituted hydroxylamine and consequently no need for deprotection of the protected acetoacetohydroxamic acid and hence no need for separation, recovery and disposal of by-products formed by these steps. The process has a further advantage for industrial production in that it is a continuous method, as opposed to the batch methods of the prior art, and gives the desired product in a high yield with a high degree of purity.

The invention is further illustrated by the following non-limiting examples, in which the reaction apparatus used is that described above in relation to the accompanying drawings. The mixer-reaction tube was a stainless steel pipe having an internal diameter of 1 mm and an outside diameter of 1.6 mm. The length of the reaction tube was 60 cm and its internal volume was thus 0.47 ml.

EXAMPLE 1

Methanol was added to 0.84 g (10 mmoles) of diketene to give 13 ml of a solution. Meanwhile, 0.84 g (12 mmoles) of hydroxylamine hydrochloride was dissolved with heating in methanol, and then about 5 ml of a 2.4N methanolic solution of sodium hydroxide and phenolphthalein were added, to adjust the pH value to 8.2. The sodium chloride produced was separated by filtration and washed with methanol. The filtrate and the washings were combined to give 14 ml of a solution containing free hydroxylamine. The mixer-reaction tube was placed in a cooling bath and maintained at 0°–1° C. with ice. The diketene solution and the hydroxylamine solution prepared as described above were then pumped simultaneously through the feeding tubes at the same rates, such that the retention period of the reagents in the mixer-reaction tube was about 10 seconds. The temperature inside the tube, determined by a thermocouple thermometer, was 2°–3° C. at this time. In the tube, the reagents reacted together to produce acetoacetohydroxamic acid.

The product coming from the terminal end of the mixer-reaction tube was collected for a period of 9 minutes directly in a reaction vessel containing 5 ml of concentrated hydrochloric acid and 5 ml of methanol and maintained at a pH value no greater than 1. The mixture was then refluxed for 30 minutes and, at the end of this time, the mixed solvent was distilled off under reduced pressure. To the residue were added 5 ml of water, and the mixture was extracted 3 times, each time with 20 ml of diethyl ether. The extracts were combined and dried over anhydrous sodium sulphate. The solvent was removed by evaporation under reduced pressure, and then the residue was purified by column chromatography through silica gel, eluted with a 1:1 by volume mixture of diethyl ether and hexane, to give 0.79 g (yield 80%) of 3-hydroxy-5-methylisoxazole, in the form of colourless crystals melting at 83°–84° C.

EXAMPLES 2 TO 5

The procedures described in Example 1 were repeated, except that the bath temperature and the reaction temperature were changed. These temperatures and the results obtained are given in the following Table.

TABLE

| Example No. | Bath temp. (°C.) | Reaction temp. (°C.) | Amount of product (g) | Yield (%) |
| --- | --- | --- | --- | --- |
| 2 | −15 | −14 to −12 | 0.77 | 78 |
| 3 | 10 | 12 to 13 | 0.76 | 77 |
| 4 | 20 | 21 to 22 | 0.75 | 76 |
| 5 | in air (15) | 39 to 40 | 0.71 | 72 |

EXAMPLE 6

The procedures described in Example 1 were repeated, except that the acidic mixture in the dehydration and cyclisation reaction vessel comprised 1 g of concentrated sulphuric acid and 10 ml of methanol giving 0.80 g (yield 81%) of 3-hydroxy-5-methylisoxazole.

EXAMPLE 7

The procedures described in Example 1 were repeated, except that a hydroxylamine solution was prepared by dissolving 0.84 g of hydroxylamine hydrochloride in 6 ml of methanol, adding 1.22 g of triethylamine and methanol to a total volume of 14 ml, giving 0.82 g (yield 83%) of 3-hydroxy-5-methylisoxazole.

EXAMPLE 8

0.84 g of diketene was added to a solution of 0.84 g of hydroxylamine hydrochloride in 8 of methanol and then further methanol was added to give 10 ml of a mixed methanolic solution of diketene and hydroxylamine hydrochloride. Meanwhile, methanol was added to 1.2 g of triethylamine to make a 10 ml solution. The respective solutions prepared above were continuously fed through the feeding tubes to effect the reaction, followed by treatment with acid as in Example 1, giving 0.73 g (yield 74%) of 3-hydroxy-5-methylisoxazole.

We claim:

1. A process for preparing 3-hydroxy-5-methylisoxazole, consisting essentially of continuously reacting diketene with unsubstituted hydroxylamine to form a reaction mixture containing acetoacetohydroxamic acid and quickly acidifying to produce said 3-hydroxy-5-methylisoxazole.

2. The process as claimed in claim 1, wherein the reaction of diketene and hydroxylamine is effected at a temperature from −15° to 25° C.

3. The process as claimed in claim 1, wherein the reaction is effected by feeding diketene and hydroxylamine continuously to a mixer-reaction tube.

4. The process as claimed in claim 3, wherein the reaction is effected using diketene or a methanolic solution thereof and a methanolic or aqueous solution of hydroxylamine.

5. The process as claimed in claim 1, wherein the reaction of diketene and hydroxylamine is effected by continuously reacting an alkaline solution with a mixed solution of diketene and an acid addition salt of hydroxylamine.

6. The process as claimed in claim 5, wherein the mixed solution of diketene and the acid addition salt is a methanolic solution.

7. The process as claimed in claim 1, wherein the retention time of hydroxylamine with diketene prior to acidification is 1 minute or less.

8. The process as claimed in claim 7, wherein said retention time is from 10 to 20 seconds.

* * * * *